United States Patent
Bart (10) Patent No.: US 11,182,411 B2
(45) Date of Patent: Nov. 23, 2021

(54) COMBINED DATA DRIVEN AND KNOWLEDGE DRIVEN ANALYTICS

(71) Applicant: Palo Alto Research Center Incorporated, Palo Alto, CA (US)

(72) Inventor: Evgeniy Bart, Santa Clara, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 329 days.

(21) Appl. No.: 16/145,869

(22) Filed: Sep. 28, 2018

(65) Prior Publication Data

US 2020/0104412 A1 Apr. 2, 2020

(51) Int. Cl.
| | |
|---|---|
| *G06F 16/31* | (2019.01) |
| *G06F 16/335* | (2019.01) |
| *G16H 10/60* | (2018.01) |
| *G06N 5/00* | (2006.01) |
| *G06N 20/00* | (2019.01) |

(52) U.S. Cl.
CPC .......... *G06F 16/313* (2019.01); *G06F 16/335* (2019.01); *G06N 5/00* (2013.01); *G06N 20/00* (2019.01); *G16H 10/60* (2018.01)

(58) Field of Classification Search
CPC ..... G06F 16/313; G06F 16/335; G16H 10/60; G06N 20/00; G06N 5/00

USPC ......................................................... 707/736
See application file for complete search history.

(56) References Cited

U.S. PATENT DOCUMENTS

| | | | |
|---|---|---|---|
| 9,092,802 B1* | 7/2015 | Akella | G06Q 30/0256 |
| 10,671,703 B1* | 6/2020 | McNair | G06F 19/328 |
| 2014/0201126 A1* | 7/2014 | Zadeh | A61B 5/165 |
| | | | 706/52 |
| 2014/0222746 A1* | 8/2014 | Gobert | G09B 5/02 |
| | | | 706/47 |
| 2014/0279837 A1* | 9/2014 | Guo | G06F 16/256 |
| | | | 707/603 |
| 2017/0006135 A1* | 1/2017 | Siebel | G06N 5/003 |
| 2018/0315507 A1* | 11/2018 | Mortazavi | G16H 50/30 |
| 2019/0005200 A1* | 1/2019 | Zimmerman | G06N 20/00 |
| 2019/0131016 A1* | 5/2019 | Cohen | A61B 6/5217 |
| 2019/0147128 A1* | 5/2019 | O'Connor | G16H 30/20 |
| | | | 703/11 |
| 2020/0050586 A1* | 2/2020 | Pal | G06F 16/13 |
| 2020/0104733 A1* | 4/2020 | Bart | G16H 50/20 |

* cited by examiner

*Primary Examiner* — Dung K Chau
(74) *Attorney, Agent, or Firm* — Womble Bond Dickinson (US) LLP (57) ABSTRACT

Systems and methods described receiving a set of example data and a set of knowledge based data and combine the set of example data and the set of knowledge based data to generate a set of combined data. The combined set can be used to train a machine learning model based on the set of combined data. The machine learning model is applied to a new set of received data for a new subject.

18 Claims, 5 Drawing Sheets

COMBINED DATA DRIVEN AND KNOWLEDGE DRIVEN ANALYTICS

TECHNICAL FIELD

Implementations of the present disclosure relate to data analytics.

BACKGROUND

The use of data analytics can improve the accuracy or diagnosis, identification, prognosis, or other predictions in a variety of environments. These techniques can include hard coded decision trees, automatic machine learning, or other uses of data to provide a predictive outcome.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

Described herein are systems that utilize knowledge driven and data driven analytics to improve the quality of analysis performed. Separately, both knowledge driven and data driven analytics can provide useful information. However, each can have drawbacks based on the type of information and how it is used. Systems described herein can take benefits of each type of analytical approach to generate models with improved predictive capabilities.

Knowledge driven approaches to analytics use accumulated knowledge from a number of sources to generate an output. For example, knowledge based data may come in the form of text books, industry papers, journal articles, online information, databases, or other repositories where knowledge of one or more subjects is stored. While many implementations can be used, knowledge driven analytics can be understood as codifying the knowledge stored in such repositories into an expert system. In some implementations, an industry expert can be used to generate the expert system or it can be learned automatically based on relations of terms in text. While this type of knowledge driven approach is useful, it is limited by the amount of knowledge available and the type of decisions it can make. For example, a question-answer type expert system learned automatically from textual data can lack the semantics necessary to make active decisions based on new data. The amount of time to provide semantic grounding can be substantial and prone to errors or incompleteness. Furthermore, knowledge based data is limited to the knowledge from which it is generated. Thus, in many industries there may be substantia knowledge gaps that prevent a system from providing additional insight beyond what an expert would know.

Data driven analytics, on the other hand, can provide additional insight by generating a machine learning model based on example data. For example, in a medical context, a machine learning system can take in a large number of hospital admissions records tagged with particular outcomes and generate a model that can predict outcomes based on those records. The model can then be applied to new admissions records to predict an outcome of newly admitted patients. While such data driven approaches overcome some of the shortcomings of knowledge driven systems, they may suffer from a complementary set of shortcomings. For example, the machine learning approach disregards the available insight from existing domain knowledge. Thus, in a medical context, research and learning from experts in fields is disregarded when generating a model. Given sufficient data, such knowledge could in principle be learned automatically. However, the resources taken to train such a model could be significant. Furthermore, machine learning models can make mistakes based on statistical anomalies. For example, even with a large set of data, rare occurrences within the system can cause spurious connections to form within the model. For example, in the medical context, a machine learning model may connect a rare disease with another condition if by random distribution the other condition happens to be present among the few examples with the rare disease. While a knowledge-driven approach will generate a system that does not connect knee replacements to a rare form of cancer, if those patients having the rare form of cancer also had a knee replacement, the machine learning model may connect the two. This can result in inaccurate output from the machine learning model.

Based on the systems that train machine learning models, data-driven approaches do not allow automatically extracting and including existing knowledge into the decision process. More accurate models could be generated (potentially with less training data) if the machine learning model used accumulated knowledge to improve the model. Performing such improvements manually may not be possible. For example, the machine learning model may have a number of elements that generate an output based on new input. However, there may be no clear connection between one element of the machine learning model and how that effects that output based on certain inputs.

The described systems and methods improve the operation of computer systems by generating models that use data-driven analytics, but also the knowledge available in a field. While generally described with reference to medical data, the systems and methods described can also be applied to other fields. For example, machine learning models can be generated by similar systems to predict mortgage defaults, stock prices, student admissions, astrophysics identification, high energy physics predictions, fleet maintenance, or other fields with sufficient example data to train a machine learning system and sufficient recorded knowledge to improve those models.

Machine learning systems described herein utilize both data-driven and knowledge based approaches to generate models that exploit the advantages of each. In some embodiments, knowledge based text data are mined to find co-occurrences of terms. For example, medical texts can be mined to find co-occurrences of various medical diagnoses.

The mining process generates a subset of existing medical knowledge. In addition, a set of training data is used to identify other pertinent information. For example, the training data can include a large number of medical diagnoses, procedures, and outcomes. In some embodiments, the pertinent information identified from the training set also includes co-occurrences of diagnoses. Ultimately, a machine learning model is generated to predict outcomes from the input data. The machine learning model can use co-occurrences of diagnoses from both the medical texts and the example data to make fewer mistakes compared with a data-driven only model. Unlike purely knowledge-driven approaches, this automatically maps real-world data available at the hospital to patient outcomes. The machine learning model can than receive new data and generate a predictive outcome based on the new data. The model can also provide new insights from data associations that may not be recorded in the knowledge based data.

Figure 1:
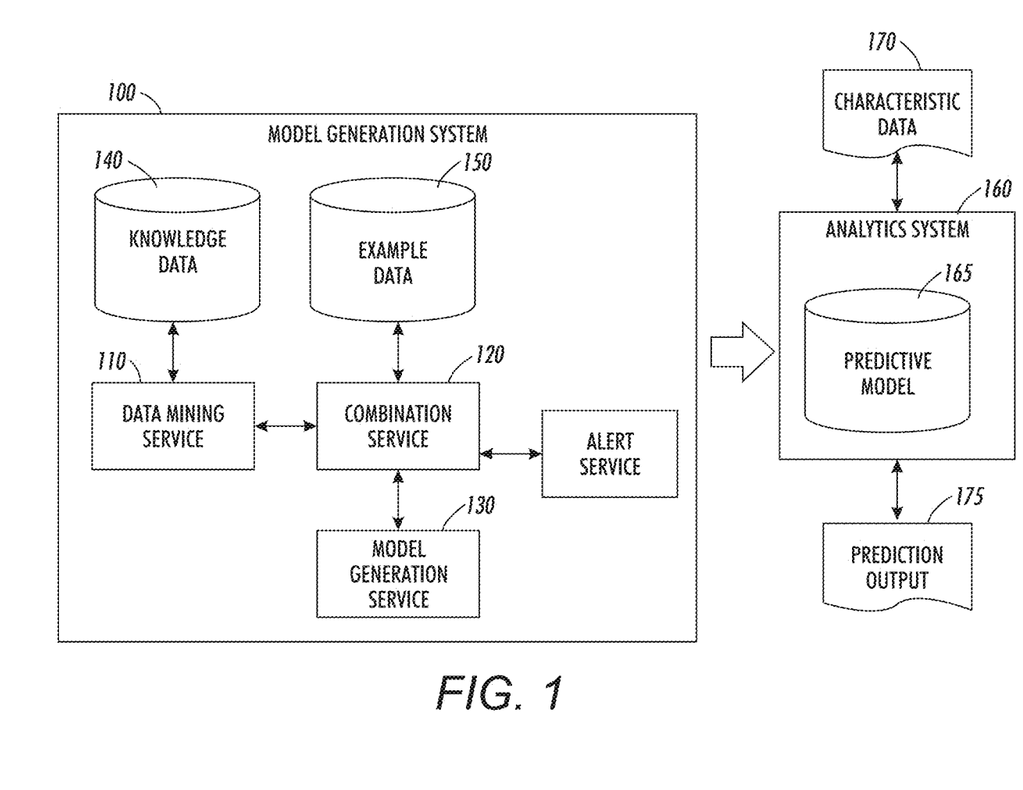
FIG. 1 is a schematic diagram of an embodiment of systems to generate and apply a machine learning model, which can be used in accordance with some embodiments.

FIG. 1 is a diagram showing a model generation system 100 and an analytics system 160. The model generation system 100 generates a predictive model 165. The predictive model 165 can then be used by the analytics system 160 to generate a prediction 175 based on a characteristic data 170. In some embodiments the characteristic data 170 can be an admission record for a patient at a hospital and the prediction 175 can be a likelihood of certain outcomes for the patient. For example, the prediction 175 can be a likelihood of readmission within a certain amount of time, an identification of another potential diagnosis, or other information that can be used by a healthcare worker to improve care for a patient.

The model generation system 100 includes knowledge data 140 and example data 150. The knowledge data 140 can be data that includes a record of expert knowledge or other information about a relevant topic. The knowledge data 140 can be in the form of human-readable text (for example, textbooks or research articles), or it can be in some other suitable format (for example, a computerized database that includes known associations between genes and medical disorders). For example, in the medical context, knowledge data 140 can include medical textbooks, journal articles, internet articles, or other data sources that include a record of knowledge about a certain field. The example data 150 can include examples of records associated with the field. For example, in the medical context, the example data 150 can include a large set of hospital admission data. The admission data can include one or more medical diagnosis codes, procedure codes, patient data, or the like. In some embodiments, the example data 150 can also include one or more flags to be used when training a predictive model 165. For example, admission data for patients can be flagged as resulting in certain outcomes, such as readmission with a certain period of time after release of a patient.

In some embodiments, the model generation system 100 includes a data mining service 110. The data mining service 110 generates a set of data from the knowledge data 140 that can be used to train a machine learning model. In some embodiments, the data mining service 110 identifies diagnostic codes, outcomes, diseases, conditions, procedures, or other medical data within the knowledge data 140 in order to form groups of useable data for training. In some embodiments, the data mining service 110 may weight one or more of the identified data elements within the knowledge data 140 differently based on the context. For example, the data mining service can perform analysis to change weighting of identified relationships between different diagnosis codes based on textual analysis. Thus, if the two terms are far apart in a document and potentially unrelated, the relationship may have a lower weight than a one where the two terms are in the same sentence. Other rules and analysis techniques can also be used. For example, structural rules using sentence templates can be used to identify those instances where the terms are highly correlated or have a specific relationship of interest. As one example, instances where the terms are related with "cause," "effect," "leads to," or the like between the words may be given a higher weight.

The data mining service 110 can therefore generate a set of relevant facts known in in the field. In some embodiments, these facts may be sets of terms. In the medical context, the terms can be limited to those that are related to diagnosis codes, procedure codes, or the like. In some embodiments, the model generation system 100 can train a machine learning model without data mining service 110. For example, the model generation system 100 can train a machine learning model from raw knowledge data 140.

In some embodiments, the model generation system 100 also includes combination service 120 that combines the knowledge data 140 and the example data 150. For example, the combination service 120 can use the output of the data mining service 110 and the example dat1 150 to generate a set of data for use by the model generation service 130. In some embodiments, the combination service 120 can replicate certain instances from either the knowledge data 140 or the example data 150 to reflect relative weighting of such instances. For example, if an instance in knowledge data 140 is identified by the data mining service 110 as having a strong correlation between certain words, it can be weighted higher than other instances. In order to have the model generation system 100 consider the instance at a higher weight, it can be provided to the model generation service 130 multiple times. In some embodiments, the combination service 120 can provide additional weighting to different instances. For example, in some embodiments, all of the knowledge data 140 or all of the example data 150 can be weighted higher than the other set of data. In some embodiments, as discussed below, the combination service 120 can be used to confirm or reject models output by the model generation service 130.

The model generation service 130 trains a machine learning model based on the knowledge data 140 and the example data 150 as provided through one or more of the data mining service 110 and the combination service 120. In various embodiments, a number of different machine learning techniques can be used by the model generation service 130. For example, in some embodiments, the model generation service 130 performs topic modeling to identify groups of terms in the data that are related. The grouping of terms can then be used to determine a likelihood of certain terms when other terms are present. For example, the model generation service 130 can treat data instances from the knowledge data 140 and example data 150 as a set of diagnostic, procedure, or other medical codes. The model generation service 130 can then determine different groupings of those codes, which can be referred to as topics. The terms in the groups of codes can have an associated probability indicating how related they are to that particular group. During training, the model generation service 130 can change those probabilities based on how often different terms co-occur in the data. As training progresses, the predictive model 165 converges and those probabilities become indicative of the likelihood of the co-occurrence of terms in the groups.

Using example data 150 by the model generation service 130 without the use of knowledge data 140 can result in misidentification of certain groupings due to limitations of the data-set. Thus, mining the knowledge data 140 and combining the data with the example data 150 prevents spurious correlations in the data by providing additional information for training. Furthermore, as knowledge data 140 can have gaps, using example data 150 to train the predictive model 165 can identify correlations that are not present in the knowledge data if there are sufficient co-occurrences in the data.

In some embodiments, the model generation service 130 can perform different types of machine learning model training. As discussed above, the model generation service 130 can perform topic modeling. In some embodiments, the topic modeling may be performed as latent dirichlet allocation (LDA), probabilistic latent semantic analysis, or other topic modeling. In some embodiments, the model generation service 130 can generate a neural network or other types of model as well. For example, the example data 150 can have one or more flags for different outcomes and the model generation service 130 can be trained to predict those outcomes based on the inputs of new data. For example, in some embodiments, the model generation service 130 can train a predictive model 165 to determine the likelihood of readmission to a hospital in view of admissions data for a new patient.

The predictive model 165 generated by the model generation system 100 can be used by an analytics system 160 to predict outcomes based on characteristic data 170. The analytics system can receive characteristic data 170 from an internal or external system. For example, the characteristic data 170 could be hospital admission data for a new patient. In some embodiments, the analytics system 160 can be hosted on the same computer system as the model generation system 100, or it can be hosted on a different device. For example, in some embodiments, the model generation system 100 can be hosted in a server system and the predictive model and analytics system 160 can be hosted on a local system. In some embodiments, the analytics system 160 can be hosted on a personal computer, laptop, tablet, phone, or other computing device in a room of a hospital where an output can be provided to a medical practitioner.

The analytics system 160 can apply the predictive model 165 to the received characteristic data 170 in order to generate a prediction output 175. In some embodiments, the predictive model 165 is a neural network that receives characteristic data 170 and extracts features to generate an output. In some embodiments, the predictive model 165 is a topic model that includes groups of terms in a number of topics. To apply the predictive model 165, the analytics system 160 can extract terms present in the characteristic data 170 and identify additional terms that may be related to the characteristic data 170 based on how correlated the terms in characteristic data 170. For example, for a term in the characteristic data, there can be a corresponding term associated with one or more topics of the predictive model 165. Based on a probability with which that term is associated with the topic, the analytics system 160 can determine other related terms. As applied to each of the terms in the characteristic data 170, the analytics system can generate a set of terms that are predicted to also be associated with the source of the characteristic data. This can be used to generate a prediction output 175.

In the context of medical diagnostics, the characteristic data 170 can include a number of diagnosis, procedures, or other information about a patient. For example, in some embodiments, the information can be received through admission data at a hospital. The analytics system 160 can then use the predictive model 165 to determine other diagnosis, procedures, or outcomes that have high probability of co-occurrence with the characteristic data 170 for the patient. For example, if the characteristic data 170 indicates a high probability of co-occurrence with a readmission, death, heart attack, or other negative consequence, that outcome can be provided to a medical practitioner to provide guidance for further treatment of the patient. In some embodiments, the prediction outcome 175 can provide predicted outcomes, potentially related conditions, or other information. The analytics system 160 can then provide the prediction output 175 to the medical practitioner. In some embodiments, the analytics system 160 can provide an output as an alert for high risk patients or as an indication of the likelihood of certain events. For example, the analytics system 160 can provide an output as a probability that a patient will be readmitted to the hospital within a period of time based on the application of the predictive model 165 to the characteristic data 170. In some embodiments, the analytics system 160 can provide the prediction outcome 175 in a computer application, an email, automated text or telephone calls, printed output on admission charts for the patient, or in other formats through which to inform a medical practitioner of the output. While the outputs are discussed with respect to medical environments, in other fields additional relevant outputs could be provided. For example, the likelihood of a mechanical failure in a system, likelihood of student success at a college, or other predictions to inform an expert of the analysis results.

Figure 2:
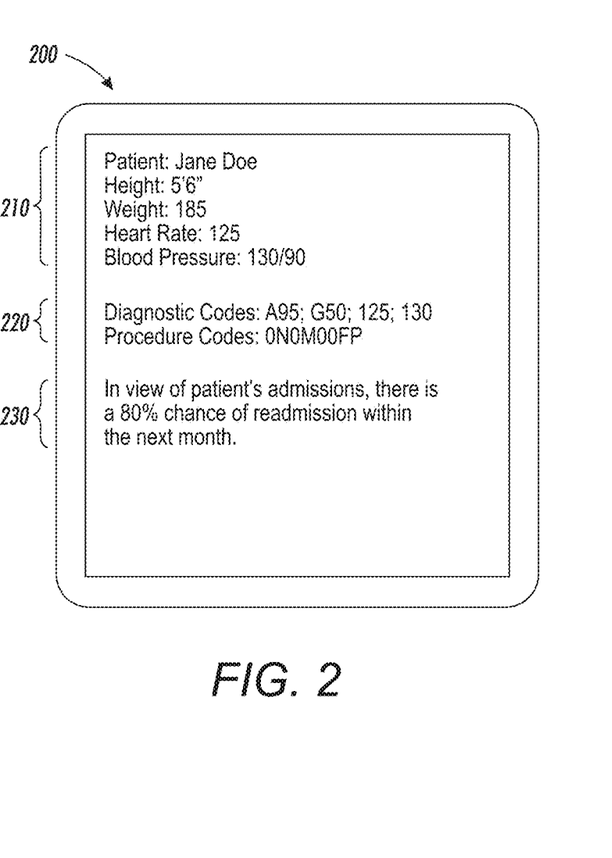
FIG. 2 is an example interface generated by an analytics system, in accordance with some embodiments.

FIG. 2 illustrates an example interface 200 generated in response to a predictive outcome for a medical admission. In some embodiments, the example interface 200 can include admission information 210, diagnostic and procedure codes 220, and a predictive outcome 230. As described with reference to FIG. 1, one or more of the admission information 210 and the diagnostic and procedure codes 220 can be used as characteristic data 170 by an analytics system 160. For example, in some embodiments, the analytics system 160 can apply the predictive model 165 to the diagnostic and procedure codes 220 to generate a prediction about an outcome for a patient.

In some embodiments, only portions of the admission information 210 and the diagnostic and procedure codes 220 may be used to generate an outcome. Furthermore, in some embodiments, the data in the admission information 210 can be modified as an input to a machine learning model. For example, a patient's blood pressure can be characterized as high or low and used as a characteristic to provide to the machine learning model. Other characterizations can also be made such as calculating a person's body mass index, high or low heart rate, or other data for input to the machine learning model. Furthermore, in some embodiments, only the diagnostic or procedure codes 210 may be provided to the machine learning model.

Based on an output of a machine learning model based on the admission information 210 or the diagnostic and procedure codes 220, an analytics system can provide an indication 230 of a potential outcome for a patient. As shown in interface 200, the example prediction is that there is an 80% chance of readmission within the next month for the patient. As presented to a medical practitioner, this can help convince the medical practitioner to further analyze the medical records of the patient, keep the patient admitted, perform additional tests, or otherwise improve treatment of a patient. In some embodiments, fewer or additional details may be provided than as shown in the interface 200. For example, in some embodiments, the probability of an outcome may not be provided and instead just an indication to perform further tests can be given. Furthermore, in some embodiments, additional potential diagnosis or recommended procedures can be provided as part of the predicted outcome 230.

Figure 3:
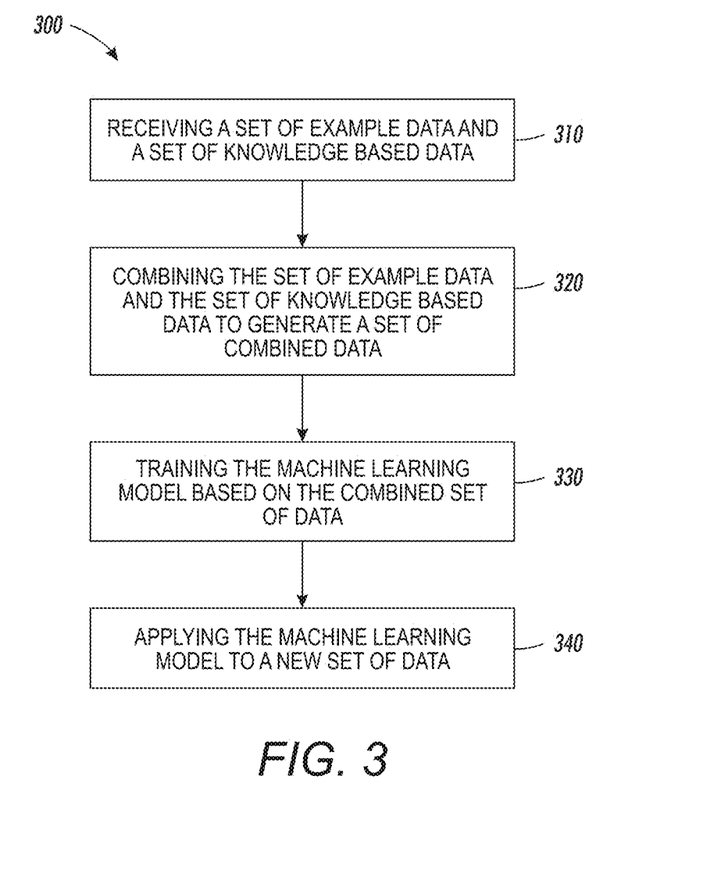
FIG. 3 is a flow diagram of an embodiment of a method of generating and applying a machine learning model, in accordance with some embodiments.

FIG. 3 is a flow chart 300 illustrating example operations of a model generation system. For example, the processes described with reference to FIG. 3 may be performed by a model generation system 100 as described with reference to FIG. 1. Beginning at block 310, the model generation system receives a set of example data and a set of knowledge based data. For example, the example data may be representative of real world outcomes for a system that the model generation system is modeling. The knowledge based data can be textual or non-textual information describing the field in which that system operates. For example, in the medical context, the example data can include patient admission charts or similar documents that describe characteristics of a patient. The example data can also include an outcome that results during or after treatment of the patient, additional diagnosis for the patient that are later discovered, or other tags that can be used to train a model. The knowledge based data can include medical textbooks, online articles, published journal articles, a combination of text sources, non-text sources such as computer databases, or the like.

In block 320, the model generation system can combine the set of example data and the set of knowledge based data to generate a set of combined data. Combining the data can include analyzing the knowledge based data to identify co-occurrences of different terms. For example, in the medical context, diagnosis or procedures that co-occur within the texts can be identified. In some embodiments, those terms can then be converted to diagnosis codes or procedure codes that match with the example data. The combined set of data can be organized into groups that can be used to train a model. In some embodiments, certain groups can be duplicated in the combined data set to increase their weighting within the generated model. In some embodiments, other weighting techniques can be used when training the model.

In block 330, a model generation system trains a machine learning model based on the combined dataset. In some embodiments, this can include topic modelling to identify certain terms that have higher probabilities of co-occurrences within documents of the combined data set. In some embodiments, training the system can include training a neural network, or other machine learning model, based on the data and one or more tags for certain inputs. In some embodiments, training a machine learning model can include generating a model based on the example data portion of a data set and identifying support for the generated model within the knowledge based portion of the data set. Thus, the knowledge based data can be used by a model generation system to check the accuracy of a model generated by the example data.

In block 340, the system can apply the machine learning model to a new set of data. Applying the model to the new set of data can generate a predictive outcome based on that set of data. For example, in the medical context, the new set of data can be an admission chart for a new patient at the hospital. The machine learning model can then use the characteristics in the admission chart to generate an outcome. For example, the outcome can include a likelihood of readmission, a likelihood that the patient has a particular diagnosis, or the likelihood of other medical outcomes.

Figure 4:
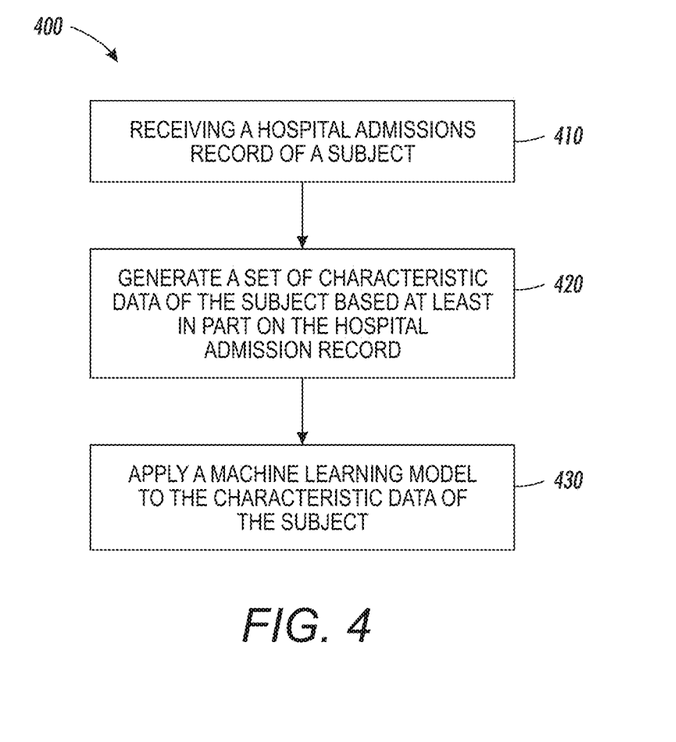
FIG. 4 is a flow diagram of an embodiment of a method of applying a machine learning model, in accordance with some embodiments.

FIG. 4 is a flow chart 400 illustrating example operations of an analytics system. For example, the processes described with reference to FIG. 4 may be performed by an analytics system 160 as described with reference to FIG. 1. Flow chart 400 is described within the context of applying an analytics system to medical records, however, similar operations could be used to analyze data in other fields.

Beginning in block 410, the analytics system receives a hospital admissions record of a subject. The admissions record can include patient data, diagnosis codes, procedure codes, or additional information. In block 420, the analytics system can generate a set of characteristic data of the subject based at least in part on the hospital admission record. For example, the characteristic data can include data that is input to a machine learning model to generate an outcome. In some embodiments, generating the characteristic data can include generating characteristics based on the admissions chart. For example, patient data can be analyzed to identify one or more characteristics such as high body mass index, high blood pressure, low blood pressure, or other diagnostic or characteristics data that can be derived from the admission chart, but may not be included in the admissions chart.

In block 430, the analytics system can apply a machine learning model to the characteristic data of the subject. The machine learning model can be trained with example data and knowledge based data. For example, in some embodiments, the machine learning model could be one trained as described above with reference to flow chart 300 or by model generation system 100. By applying the machine learning model, the analytics system can generate a useful output. For example, if the machine learning model is a topic model, the output of the machine learning model can be a probability that certain diagnostic codes also apply to the patient. In some embodiments, a probability of readmission, death, or other information can also be provided by the analytics system.

Various operations are described as multiple discrete operations, in turn, in a manner that is most helpful in understanding the present disclosure, however, the order of description may not be construed to imply that these operations are necessarily order dependent. In particular, these operations need not be performed in the order of presentation.

Figure 5:
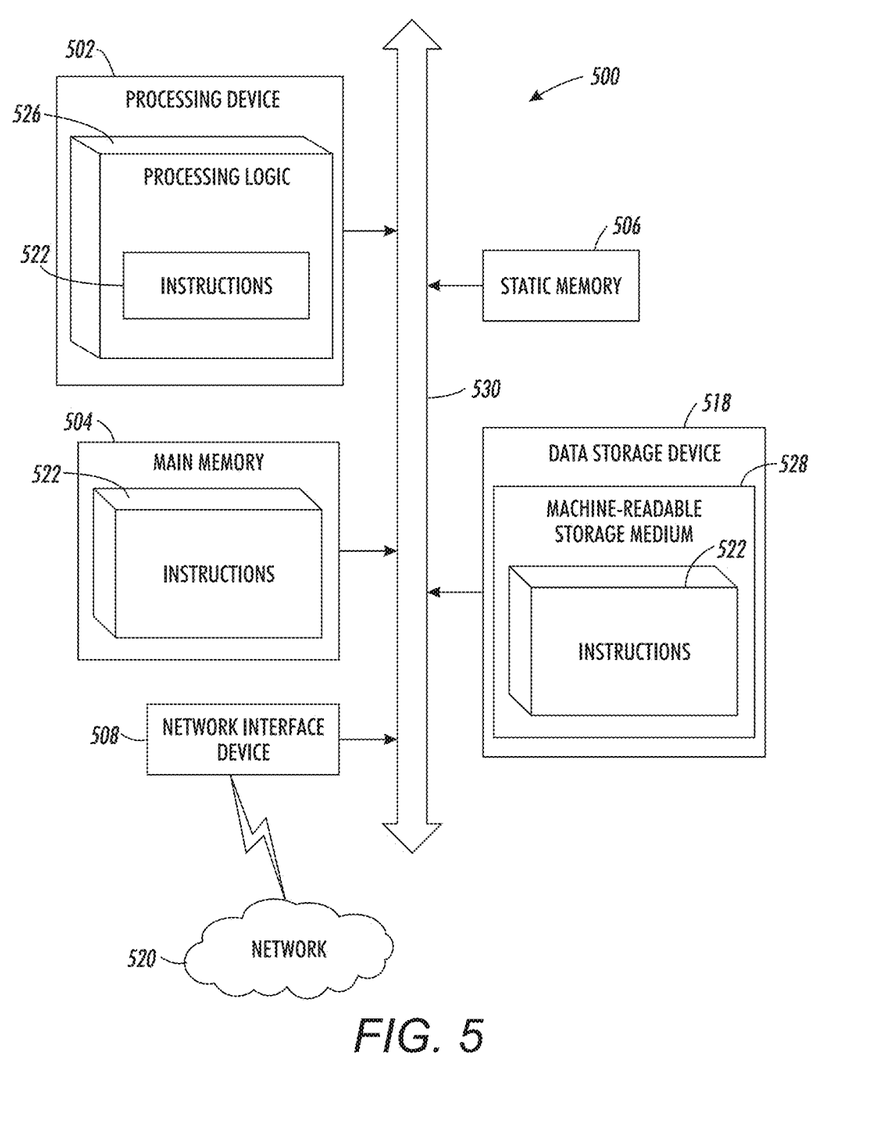
FIG. 5 is an illustration showing an example computing device which may implement the embodiments described herein.

FIG. 5 illustrates a diagrammatic representation of a machine in the example form of a computer system 500 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 500 may be representative of a server computer system, such as model generation system 100 or analytics system 160.

The exemplary computer system 500 includes a processing device 502, a main memory 504 (e.g., read-only memory (ROM), flash memory, dynamic random access memory (DRAM), a static memory 506 (e.g., flash memory, static random access memory (SRAM), etc.), and a data storage device 518, which communicate with each other via a bus 530. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 502 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute processing logic 526, which may be one example of system 400 shown in FIG. 4, for performing the operations and steps discussed herein.

The data storage device 518 may include a machine-readable storage medium 528, on which is stored one or more set of instructions 522 (e.g., software) embodying any one or more of the methodologies of functions described herein, including instructions to cause the processing device 502 to execute model generation system 100 or analytics system 160. The instructions 522 may also reside, completely or at least partially, within the main memory 504 or within the processing device 502 during execution thereof by the computer system 500; the main memory 504 and the processing device 502 also constituting machine-readable storage media. The instructions 522 may further be transmitted or received over a network 520 via the network interface device 508. In some embodiments, the data storage device, the memory, the network, the processing device, and other components may store and/or access the data, including the example data and knowledge-based data. This data may be stored in raw form or in a preprocessed form, depending on the application.

The machine-readable storage medium 528 may also be used to store instructions to perform a method for analyzing log data received from networked devices, as described herein. While the machine-readable storage medium 528 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A method comprising:
mining one or more sources of knowledge data to identify a set of knowledge based data to be used in training a machine learning model;
receiving a set of example data and the set of knowledge based data;
combining the set of example data and the set of knowledge based data to generate a set of combined data, wherein combining the set of example data and the set of knowledge based data comprises applying weights to components of the knowledge based data based on a relationship of terms in the components of the knowledge based data, wherein the relationship comprises corresponding locations of the components within the knowledge based data;
training the machine learning model based on the set of combined data; and
applying the machine learning model to a new set of data.

2. The method of claim 1, wherein training the machine learning model comprises identifying groups of items in the example data with high probabilities co-occurrence.

3. The method of claim 1, wherein the set of example data comprises hospital admission data of a plurality of patients.

4. The method of claim 1, wherein the knowledge based data comprises one or more of medical texts or databases.

5. The method of claim 1, wherein combining the set of example data and the set of knowledge based data comprises:
identifying a set of terms in the example data;
filtering the knowledge based data based on the identified set of terms; and
generating the combined set of data based on the filtered knowledge based data and the example data.

6. The method of claim 1, wherein the machine learning model comprises one or more of a topic model, a neural network, or a latent space encoder.

7. The method of claim 1, wherein applying the machine learning model to a new set of data comprises:
identifying a set of terms in the new set of data that are associated in a group by the machine learning model; and
determining a probability that another term is associated with the new set of data based on set of terms and the group.

8. A non-transitory computer-readable medium having instructions stored thereon that, when executed by a processing device, cause the processing device to:
mine one or more sources of knowledge based medical data to identify a set of knowledge based medical data to be used in training a machine learning model;
receive a set of medical admission records of a plurality of patients and the set of knowledge based medical data;
combine the set of medical admission records and the set of knowledge based medical data to generate a set of combined data, wherein combining the set of example data and the set of knowledge based data comprises applying weights to components of the knowledge based data based on a relationship of terms in the components of the knowledge based data, wherein the relationship comprises corresponding locations of the components within the knowledge based data;
train the machine learning model based on the set of combined data; and
apply the machine learning model to a new admission record of a new patient.

9. The non-transitory computer-readable medium of claim 8, wherein training the machine learning model comprises identifying groups of items in the example data.

10. The non-transitory computer-readable medium of claim 8, wherein the medical admissions records comprise an indication of one or more diagnosis code or procedure code associated with each of the plurality of patients and an indication of an outcome associated with each of the plurality of patients.

11. The non-transitory computer-readable medium of claim 8, wherein the knowledge based data comprises one or more of medical texts or databases.

12. The non-transitory computer-readable medium of claim 8, wherein to combine the set of medical admissions records and the set of knowledge based data, the instructions further cause the processing device to:
identify a set of diagnoses or procedures in the example data;
filter the knowledge based data based on the identified set of diagnoses or procedures; and
generate the combined set of data based on the filtered knowledge based data and the medical admissions records.

13. The non-transitory computer-readable medium of claim 8, wherein the machine learning model comprises one or more of a topic model, a neural network, or a latent space encoder.

14. The non-transitory computer-readable medium of claim 8, wherein to apply the machine learning model to a new admission record, the instructions further cause the processing device to:
identify a set of terms in the new admission record that are associated in a group by the machine learning model; and
determine a probability that another term is associated with the new admission record based on set of terms and the group.

15. A system comprising:
a memory device; and
a processing device operatively coupled to the memory device, wherein the processing device is to:
mine one or more sources of knowledge data to identify a set of knowledge based data to be used in training a machine learning model;
receive a set of medical admission records of a plurality of patients and the set of knowledge based medical data;
combine the set of medical admission records and the set of knowledge based medical data to generate a set of combined data, wherein combining the set of example data and the set of knowledge based data comprises applying weights to components of the knowledge based data based on a relationship of terms in the components of the knowledge based data, wherein the relationship comprises corresponding locations of the components within the knowledge based data;
receive a hospital admission record of a subject;
generate a set of characteristic data of the subject based at least in part on the hospital admission record; and apply the machine learning model to the characteristic data of the subject, wherein the machine learning model is trained with the set of combined data.

16. The system of claim 15, wherein the processing device is further to generate an interface comprising an indication of a likelihood of an outcome for the patient.

17. The system of claim 15, wherein to apply the machine learning model, the processing device is further to:
   identify a probability of co-occurrence of a predicted diagnosis code with a diagnosis code in the characteristic data; and
   determine based on the probability of co-occurrence an indication to provide to a practitioner.

18. The system of claim 15, wherein the machine learning model comprises one or more of a topic model, a neural network, or a latent space encoder.

* * * * *